United States Patent
Veit et al.

(10) Patent No.: US 10,612,047 B2
(45) Date of Patent: *Apr. 7, 2020

(54) BIOGAS APPARATUS FOR INTEGRATION WITH AN ETHANOL PRODUCTION SYSTEM

(75) Inventors: Eberhard Veit, Crystal Lake, IL (US); Ondrej Stonawski, Crystal Lake, IL (US); Adam Halsband, Cary, IL (US)

(73) Assignee: EISENMANN CORPORATION, Crystal Lake, IL (US)

( * ) Notice: Subject to any disclaimer, the term of this patent is extended or adjusted under 35 U.S.C. 154(b) by 1275 days.

This patent is subject to a terminal disclaimer.

(21) Appl. No.: 12/764,451

(22) Filed: Apr. 21, 2010

(65) Prior Publication Data

US 2010/0317091 A1 Dec. 16, 2010

Related U.S. Application Data

(63) Continuation of application No. 12/484,576, filed on Jun. 15, 2009, now Pat. No. 8,669,083.

(51) Int. Cl.
| | |
|---|---|
| *C12M 1/36* | (2006.01) |
| *C12M 1/00* | (2006.01) |
| *C12P 7/10* | (2006.01) |
| *C12P 5/02* | (2006.01) |
| *C12M 1/107* | (2006.01) |

(52) U.S. Cl.
CPC ............... *C12P 7/10* (2013.01); *C12M 21/04* (2013.01); *C12M 21/12* (2013.01); *C12M 43/02* (2013.01); *C12P 5/023* (2013.01); *Y02E 50/16* (2013.01); *Y02E 50/17* (2013.01); *Y02E 50/343* (2013.01)

(58) Field of Classification Search
CPC .............................. C12M 21/04; C12M 21/12
USPC ......................................................... 435/165
See application file for complete search history.

(56) References Cited

U.S. PATENT DOCUMENTS

| | | | |
|---|---|---|---|
| 5,316,782 A * | 5/1994 | Zimlich, III | 426/624 |
| 5,662,810 A * | 9/1997 | Willgohs | 210/781 |
| 2008/0050800 A1* | 2/2008 | McKeeman et al. | 435/262.5 |
| 2009/0093027 A1* | 4/2009 | Balan et al. | 435/99 |
| 2009/0250401 A1* | 10/2009 | Kotelko et al. | 210/695 |

* cited by examiner

*Primary Examiner* — Nghi V Nguyen
(74) *Attorney, Agent, or Firm* — Burris Law, PLLC

(57) ABSTRACT

An integrated system produces ethanol and biogas from raw plant materials. The system includes a pretreatment apparatus for converting raw plant materials into sugars and a fermenter for fermenting the sugars to produce a beer including ethanol. A distillation apparatus separates the beer into the ethanol and a whole stillage, and a separator then separates the whole stillage into a thin stillage and wet distillers grains. A biogas apparatus processes a first portion of the thin stillage to produce biogas and a biogas effluent, and converts a percentage of the non-fermentable solids and organic acids in the thin stillage into biogas. The pretreatment apparatus is supplied with an amount of fresh water and an amount of backset, the backset including the biogas effluent recycled from the biogas apparatus to the pretreatment apparatus.

22 Claims, 4 Drawing Sheets

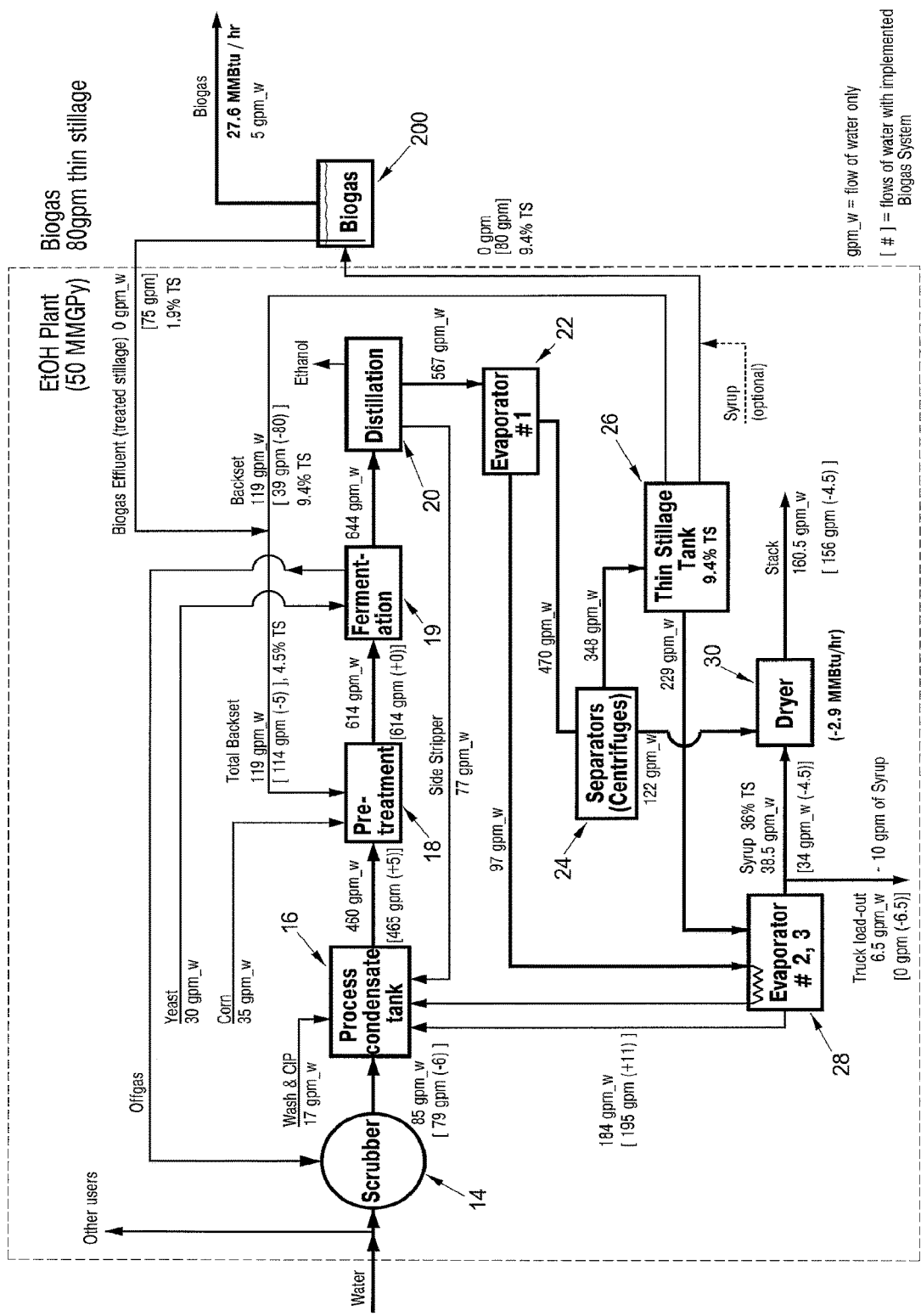
Fig. 1 Backset Clean-up + Syrup Load-out Elimination

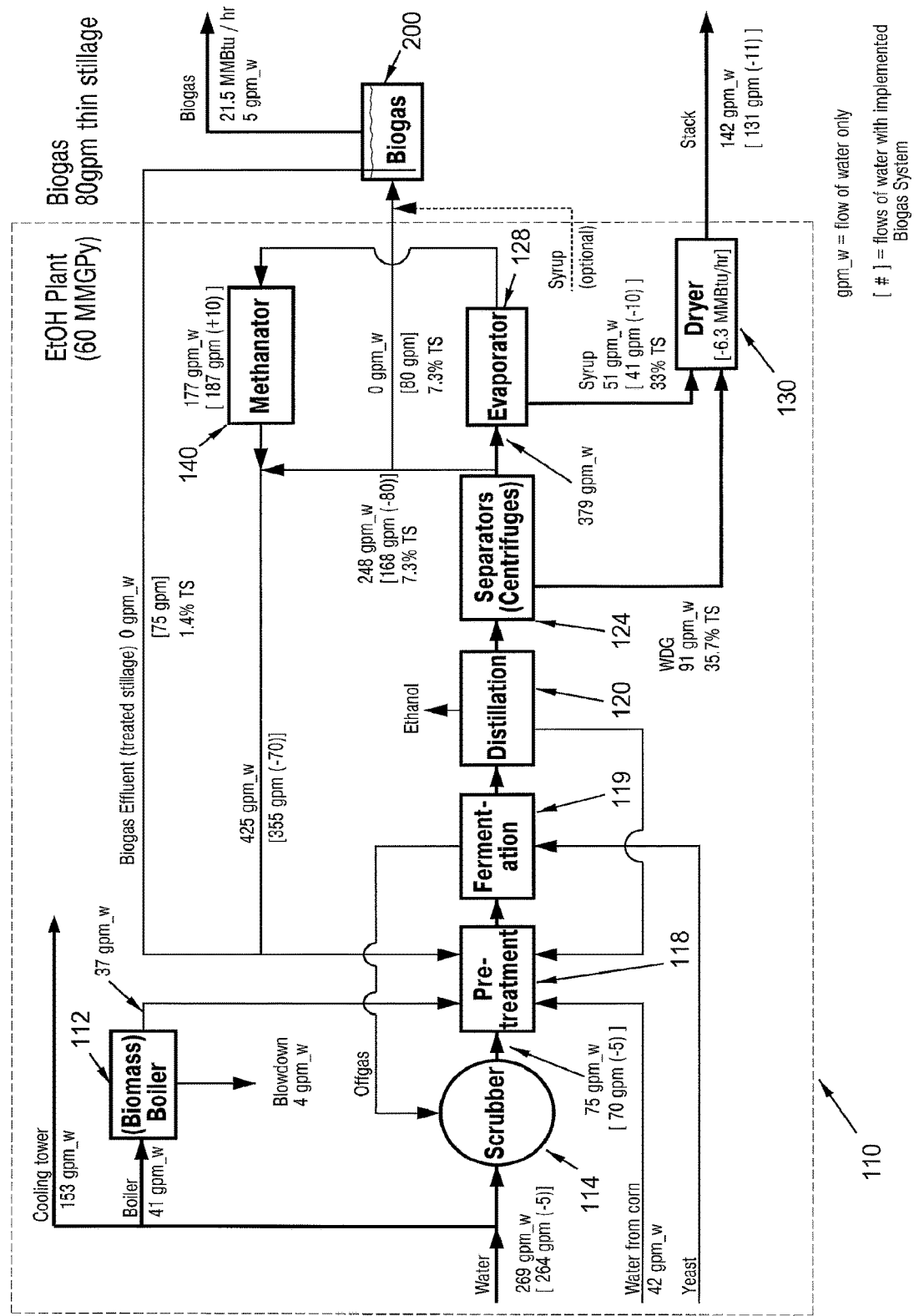
Fig. 2a Biogas System Used for Backset Clean-up

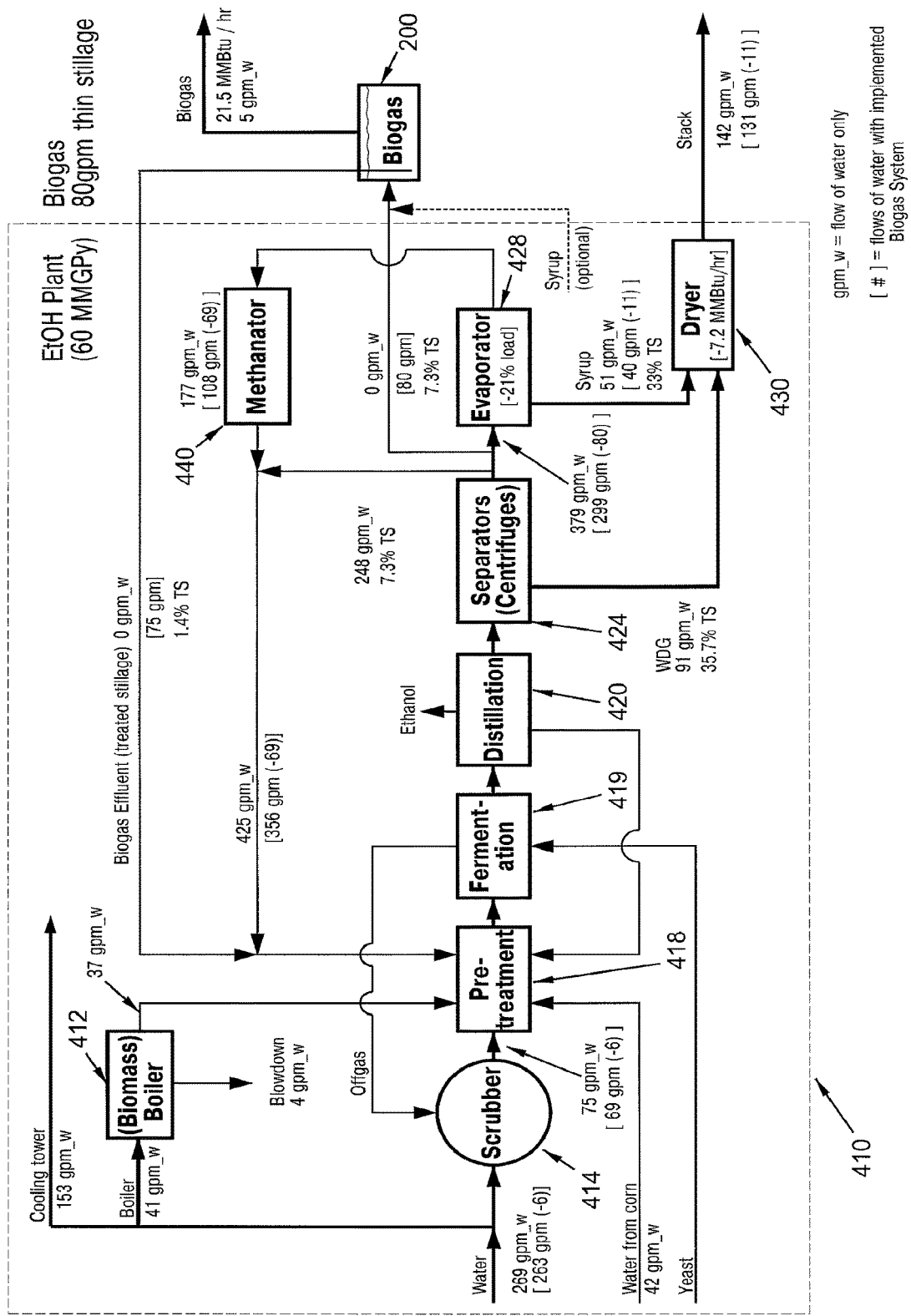
Fig. 2b Biogas System Used for Evap or Dryer Load Reduction

BIOGAS APPARATUS FOR INTEGRATION WITH AN ETHANOL PRODUCTION SYSTEM

FIELD

The disclosed apparatus and process relates to the production of ethanol from fermentation of sugars, or sugars derived from starches or converted cellulosic material. More particularly, the disclosed apparatus and process relates to anaerobic digestion of byproducts of the ethanol production process to generate biogas and to render the byproducts more readily recyclable into the ethanol process, thereby improving the energy efficiency and throughput of the ethanol production process and reducing or eliminating the need to dispose of wastewater and other byproducts.

BACKGROUND

An ethanol plant typically produces ethanol by fermentation of sugars using yeast. The sugars can be derived from a variety of raw plant materials. In particular, the sugars are commonly derived from sugar-containing plant materials such as sugar cane or beets, from the conversion of starch obtained from corn, other grains, or any other starch containing materials, or from the conversion of cellulosic materials.

In a typical prior art process, the raw plant materials are usually prepared in various pre-treatment steps that free the sugars. In pretreatment, water and/or backset is added to prepare the raw materials for conversion to sugar and subsequently from sugar to alcohol (i.e., ethanol) in fermentation. Backset refers to liquids, with or without solids, that are produced as a result of subsequent process steps, and are then recycled back for use in earlier process steps.

Once the sugars have been freed by pretreatment, the sugars are fermented to ethanol, and the resultant mixture of ethanol, solids, and other dissolved substances such as acids, oils, salts, and proteins, is termed beer. The beer is separated by distillation into ethanol and whole stillage, which contains a mixture of liquid, solids, solubles, and other dissolved substances. The whole stillage may then be thickened by evaporation prior to separating the liquids, solubles, and fine particles from the solids. Separation is typically done by means of a decanter centrifuge that separates the whole stillage into thin stillage (centrate) and Wet Distillers Grains (WDG). The thin stillage usually is thickened by evaporation and separated into evaporator condensate and syrup, a high-solids liquid product. The WDG can be sold as is or recombined with the syrup and sold. Most commonly, the WDG is dried, alone or along with all or a portion of the syrup, to produce Dried Distillers Grains (DDG) or Dried Distillers Grains with Solubles (DDGS), respectively. DDG and DDGS can be sold and shipped world-wide because they have an extended shelf life. DDG and DDGS are typically used in animal feed. A portion of the thin stillage is recycled into the ethanol process as backset, i.e., a portion of the thin stillage is used to offset some of the water needs of the process.

BRIEF SUMMARY

An integrated system is provided for producing ethanol and biogas from raw plant materials. The system includes a pretreatment apparatus for converting raw plant materials into sugars and a fermenter having yeast for fermenting the sugars to produce a beer comprising ethanol. A distillation apparatus separates the beer into the ethanol and a whole stillage, and a separator then separates the whole stillage into a thin stillage and wet distillers grains, the thin stillage including non-fermentable solids and organic acids. A biogas apparatus processes a first portion of the thin stillage to produce biogas and a biogas effluent. The biogas apparatus converts a percentage of the non-fermentable solids and organic acids in the thin stillage into biogas, thereby reducing the concentration of the non-fermentable solids and organic acids in the biogas effluent. The pretreatment apparatus is supplied with an amount of fresh water and an amount of backset, wherein the backset includes the biogas effluent recycled from the biogas apparatus to the pretreatment apparatus.

An integrated system is further provided for producing ethanol and biogas from raw plant materials. The system includes a pretreatment apparatus for converting raw plant materials into sugars, and a fermenter having yeast for fermenting the sugars to produce a beer comprising ethanol. A distillation apparatus separates the beer into the ethanol and a whole stillage, a separator separates the whole stillage into a thin stillage and wet distillers grains, the thin stillage comprising non-fermentable solids and organic acids, and an evaporator concentrates a first portion of the thin stillage into a syrup by boiling off vapor from the thin stillage. A biogas apparatus processes at least one of a portion of the syrup and a second portion of the thin stillage to produce biogas and a biogas effluent. The biogas apparatus converting a percentage of the non-fermentable solids and organic acids in the syrup and the thin stillage into biogas, thereby reducing the concentration of the non-fermentable solids and organic acids in the biogas effluent. The pretreatment apparatus is supplied with an amount of fresh water and an amount of backset, wherein the backset comprises the biogas effluent recycled from the biogas apparatus to the pretreatment apparatus.

A biogas apparatus is also provided for processing thin stillage produced by an ethanol production system, for producing biogas, and for returning biogas effluent to the ethanol production system as backset. The thin stillage that is processed includes non-fermentable solids and organic acids. The biogas apparatus has at least one anaerobic digester that includes microorganisms for converting non-fermentable solids and organic acids in the thin stillage into biogas, thereby producing a biogas effluent having a reduced concentration of non-fermentable solids and organic acids. At least some of the microorganisms are adapted for an ammonia environment. In the digester, pH control is accomplished by adding ammonia to the thin stillage. Nitrogen from the ammonia is recycled to the ethanol plant in the biogas effluent backset for use as a yeast nutrient.

An integrated process is disclosed for producing ethanol and biogas from raw plant materials. The process includes: (1) fermenting sugars derived from a mixture including the raw plant materials to produce a beer comprising ethanol, the mixture comprising an amount of fresh water and an amount of backset; (2) distilling the beer into the ethanol and a whole stillage; (3) separating the whole stillage into a thin stillage and wet distillers grains, the thin stillage comprising non-fermentable solids and organic acids; (4) anaerobically digesting a first portion of the thin stillage to produce biogas and a biogas effluent by converting the non-fermentable solids and organic acids into biogas, thereby reducing the concentration of non-fermentable solids and organic acids in the biogas effluent; and (5) recycling the biogas effluent as backset.

An integrated process is further disclosed for producing ethanol and biogas from raw plant materials. The process includes: (1) fermenting sugars derived from a mixture including the raw plant materials to produce a beer comprising ethanol, the mixture comprising an amount of fresh water and an amount of backset; (2) distilling the beer into the ethanol and a whole stillage; (3) separating the whole stillage into a thin stillage and wet distillers grains, the thin stillage comprising non-fermentable solids and organic acids; (4) concentrating a first portion of the thin stillage into a syrup by boiling off vapor from the thin stillage; (5) anaerobically digesting at least one of a portion of the syrup and a second portion of the thin stillage to produce biogas and a biogas effluent by converting the non-fermentable solids and organic acids into biogas, thereby reducing the concentration of non-fermentable solids and organic acids in the biogas effluent; and (6) recycling the biogas effluent as backset.

BRIEF DESCRIPTION OF THE DRAWINGS

FIG. 1 is a schematic depicting an embodiment of an ethanol production system including a biogas apparatus for converting at least a portion of the thin stillage into biogas and a biogas effluent, wherein a portion of the backset is cleaned up and the syrup load-out is eliminated.

FIG. 2a is a schematic depicting an embodiment of an ethanol production system including a biogas apparatus for converting at least a portion of the thin stillage into biogas and a biogas effluent, wherein a portion of the backset is cleaned up.

FIG. 2b is a schematic depicting an embodiment of an ethanol production system including a biogas apparatus for converting at least a portion of the thin stillage into biogas and a biogas effluent, wherein the load on the evaporator and/or dryer is reduced.

DETAILED DESCRIPTION

Figure 3:
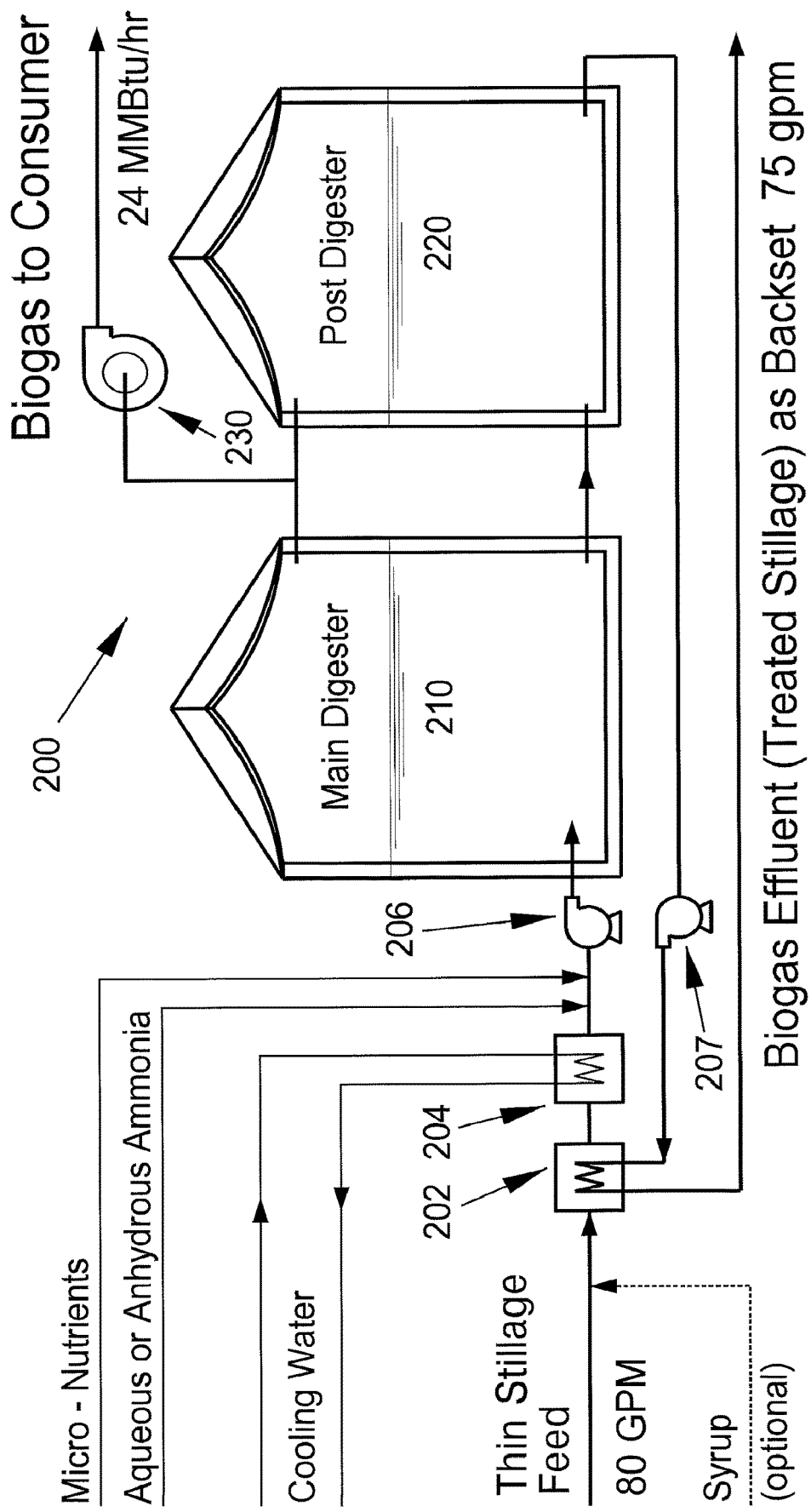
FIG. 3 is a schematic depicting an embodiment of a biogas apparatus for converting thin stillage into biogas and a biogas effluent.

The following examples further illustrate the disclosed systems and methods but, of course, should not be construed as in any way limiting their scope.

There is shown in FIG. 1 a schematic diagram and mass balance of water for an embodiment of an ethanol production system 10, including a biogas apparatus 200. The biogas apparatus 200 is integrated into the ethanol production system 10. The disclosed system and process integrates anaerobic digestion of byproducts of ethanol production, and in particular thin stillage, to produce biogas that partially offsets the energy requirements of the ethanol production system and to provide improved backset (as effluent from the biogas apparatus) that enhances the quality of the fermentation and reduces fresh water usage of the ethanol production system. Backset is understood by those in the art to describe water-containing byproducts of a process that are recycled from downstream to upstream process steps, at least in part to reduce fresh water usage. Additionally, the integrated system and process can reduce or eliminate side streams that might exist from process limitations or imbalances, to result in a zero discharge plant with respect to byproducts that must be disposed for free or at a net cost.

The ethanol production system 10 includes a pretreatment apparatus 18 in which sugars are freed from the feedstock (i.e., raw plant materials). The pretreatment apparatus 18 pretreats the raw plant materials, such as corn kernels, to free the sugars from the raw plant materials for fermentation in a fermenter 19. As shown, raw plant materials, such as corn, are provided to the pretreatment apparatus 18, along with enzymes to break down the raw plant materials. In the fermenter 19, yeast is added for fermenting the sugars derived from the raw plant materials. In addition, liquid is added to the pretreatment apparatus 18 to create a liquid mash. The liquid can include fresh water, water recovered from wash and clean-in-place processes in the plant, water recovered from evaporators (discussed below), and backset recycled from downstream steps in the process (discussed below). In addition, an amount of ammonia is typically added to the fermenter 18 as a nutrient for the yeast. As described below, nitrogen from the ammonia may be provided at least in part as recovered ammonia (i.e., as ammonia nitrogen or ammonia salts) from proteins that are anaerobically digested in the biogas apparatus 200.

In summary, the biogas apparatus and integrated ethanol and biogas production process are based on using all, or a portion of, the thin stillage produced by an ethanol production process, adjusting the pH and temperature of the thin stillage as required, and directing the thin stillage to a biogas reactor to decrease the solids and organic acid content of the thin stillage. In one embodiment, the biogas reactor includes a multi-stage anaerobic digester, the pH is neutralized, and the temperature is adjusted into a mesophilic temperature range. The anaerobic digester is inoculated with a bacterial population at initial startup. In one embodiment, an ammonia adapted bacterial population is used, and the pH is adjusted by the use of aqueous or anhydrous ammonia. Micronutrient levels are monitored and can be adjusted by the addition of a nutrient mix to maintain the health of the bacteria population. The biogas reactor digests thin stillage to produce biogas that can be used in the steam boilers or dryers to offset the use of natural gas or other hydrocarbon fuel, or can be used to generate electricity. Effluent from the biogas reactor, which has less non-fermentable solids and fermentation inhibitors than untreated thin stillage, is used as backset and returned to the front end of the ethanol process. The biogas reactor temperature can be maintained by supplying the thin stillage at an elevated temperature to accommodate for heat losses, and during shutdown periods, temperature can be maintained by steam injection or hot water heating. The biogas reactor can operate at mesophilic temperatures, or alternatively at thermophilic temperatures. The biogas effluent is reheated by heat exchange with the incoming thin stillage to recover most of the heat for the ethanol production process. The biogas effluent is recycled back into the ethanol process as backset without generating any side streams that require disposal. Further, the added ammonia and the ammonia generated from protein digestion in the biogas reactor is used as a nutrient for the yeast in fermentation. In a well balanced system, there will be no side discharge streams and the overall plant will use no additional ammonia in excess of what is already typically required for good fermentation.

As shown in FIG. 1, fresh water is supplied to a scrubber 14 and to other uses in the system 10. The scrubber 14 is used to recover ethanol from the $CO_2$ rich off-gas from the fermenter 19. Because some water will be consumed by the ethanol system 10, an amount of fresh water replenishment is typically required. In the illustrated embodiment, 85 GPM of water exits the scrubber for use in the ethanol system 10. The water from the scrubber 14 and other sources is collected in a process condensate tank 16. Ultimately, an amount of water is supplied from the process condensate tank 16 to the pretreatment apparatus 18. In the illustrated embodiment, the additional sources of water to the process condensate tank 16 include 17 GPM of wash and clean-in-place water, 281 GPM of recovered evaporator water, and 77 GPM of side stripper water recovered from distillation, and the total amount of water supplied to the pretreatment apparatus 18 form the condensate tank 16 is 460 GPM (460=85+17+281+77).

In addition, in the illustrated embodiment, the corn provides the equivalent of 35 GPM of water. Thus, including a backset flow rate of 119 GPM of water, the total amount of water provided to the pretreatment apparatus 18 is 614 GPM (614=460+35+119). Note that the corn brings a substantial amount of solids that are included in the total flow of mash input to the fermenter 19. Also, the yeast provided to the fermenter 19 is in a mixture including 30 GPM of water, so that the beer exiting the fermenter 19 includes 644 GPM of water.

Fermentation occurs at slightly elevated temperatures as compared with ambient. In the pretreatment, the corn mash is heated and combined with enzymes to break down the starches into sugars. Then, the yeast goes to work fermenting the free sugars to ethanol, until essentially all of the sugars are consumed. The resultant beer includes alcohol and a substantial amount of the corn kernel solids that are not fermentable (i.e., solids that cannot be digested by the yeast). In a typical mash, about 33% of the corn kernel solids are not fermentable. The beer also includes various substances resulting from the breakdown of the raw plant (e.g., corn) materials, such as oils, acids, salts, proteins, and soluble solids.

The beer flows from the fermenter 19 to a distillation apparatus 20, where alcohol vapors are concentrated and separated from solids. Multiple distillation columns can be used to increase the concentration of the alcohol ultimately produced by distillation. Note that distillation can only achieve about 190 proof alcohol (i.e., 95% purity). Therefore, in order to obtain 200 proof (100% pure) ethanol that is needed for many applications, including for example internal combustion engines, the alcohol is further purified by dehydration. A common method of dehydration is performed using a molecular sieve as a desiccant. Typically, the solids, in a liquid slurry termed whole stillage, are extracted from the bottom of the first distillation column. In the illustrated embodiment, out of a total water flow rate of 644 GPM into the distillation apparatus 20, 567 GPM of the water is extracted in the whole stillage. The remaining liquid (i.e., 75 GPM) is taken off in the form of ethanol.

The whole stillage flows to a first evaporator 22, to boil off some of the water, resulting in a concentrated whole stillage that can be separated into solids and liquids. The vapors extracted from the first evaporator 22 are returned to the process condensation tank 16, after the heat of evaporation is recovered via heat exchange with other evaporators (e.g., a second and a third evaporator, as shown). In the illustrated embodiment, 97 GPM of water is evaporated in the first evaporator 22 and recondensed and recycled to be fed back into the pretreatment apparatus 18, while 470 GPM of whole stillage proceeds to a separator 24.

The separator 24 typically employs one or more decanter centrifuges to separate the whole stillage into wet distillers grains (WDG) and thin stillage. The WDG is composed of coarse solids and moisture. The WDG is then sent to a dryer 30, which removes the remaining water from the WDG by heating. The resultant product from the dryer 30 is Dried Distillers Grains (DDG). Alternatively, the WDG can be combined with syrup (discussed below) in the dryer 30 to yield Dried Distillers Grains with Solubles (DDGS). In the illustrated embodiment, of the 470 GPM of water in the form whole stillage sent to the separator 24, 348 GPM of water is contained in the thin stillage while 112 GPM of water is contained in the WDG sent to the dryer 30.

The thin stillage is a liquid substance that is not completely clear, but rather includes a significant portion of solids, as fine particles, that are not fermentable (e.g., about 9.4% solids in the illustrated embodiment), as well as solubles, oils, organic acids, salts, proteins, and other substances that may inhibit yeast activity. The thin stillage is collected from the separator 24 in a thin stillage tank 26, for distribution to various uses. A portion of the thin stillage can be sent to a second evaporator 28 to be thickened into a syrup.

In one embodiment, the syrup includes about 36% total solids and is the consistency of a creamy mud. Often in prior art systems, if there is no saleable use for the syrup especially if the addition of syrup to the dryer is limited, it may be disposed of either for no profit or at a cost; however, no such disposal of syrup is required in an embodiment the presently disclosed system and process. Alternatively, or in addition, the thin stillage can be sent to the dryer 30, combined with the WDG, and dried into DDGS. In the illustrated embodiment, if no biogas apparatus 200 is used, the second evaporator 28 generates syrup containing 45 GPM of water, of which 38.5 GPM is taken off by the dryer 30 and 6.5 GPM is trucked away as load-out syrup that cannot be processed and has no other use in the system 10. When a biogas apparatus 200 is used, the second evaporator 28 generates syrup containing 34 GPM of water, all of which is sent to the dryer 30. No load-out syrup is generated in the depicted embodiment when the biogas apparatus 200 is used, and the water driven off by the dryer 30 is reduced by 4.5 GPM from 160.5 GPM to 156 GPM.

Another portion of the thin stillage can be recycled as backset to the pretreatment apparatus 18 for use in the pretreatment and fermentation processes. In the illustrated embodiment, if no biogas apparatus 200 is used, 119 GPM of water in the thin stillage is recycled to the pretreatment apparatus 18 as direct backset while 229 GPM of water in the thin stillage is sent to the second evaporator 28 for thickening into syrup. When a biogas apparatus 200 is used, only 39 GPM of water in the thin stillage is recycled as direct backset (a reduction of 80 GPM) and 80 GPM of water in the thin stillage is sent to the biogas apparatus 200. The biogas apparatus generates 27.6 mM BTU/hr of biogas and consumes 5 GPM of water in the biogas, returning 75 GPM of water as treated thin stillage backset to the pretreatment apparatus 18.

The amount of direct thin stillage that can be used as backset is often limited by the concentration of non-fermentable solids and fermentation inhibiting substances present in the thin stillage. For example, if too large a proportion of the water or liquids supplied to the pretreatment apparatus 18 is in the form of thin stillage backset, the excess non-fermentable solids and fermentation inhibiting substances can limit or decrease the net ethanol production of the system 10. The biogas apparatus disclosed herein helps to overcome this problem, both by partially purifying some of the thin stillage into a biogas effluent (i.e., treated thin stillage with substantially reduced non-fermentable solids and fermentation inhibitors) that can be used as backset and by enabling a larger amount of thin stillage to be used directly as backset due to the dilution effect obtained by using the biogas effluent as backset. Also, the partially purified biogas effluent allows for the use of more raw plant materials in the pretreatment apparatus 18, and thus more sugars in the fermenter 19, thus increasing the net ethanol production capacity of the system 10.

Yet another portion of the thin stillage can be used as a feed for the biogas apparatus 200. An embodiment of a closed loop biogas apparatus 200 is depicted schematically in FIG. 3. The biogas apparatus 200 includes a main digester 210 for anaerobically digesting the non-fermentable solids and other substances in the thin stillage, and converting those substances to biogas. The main digester 210 contains bacteria and other microorganisms that operate anaerobically (i.e., in the absence of oxygen) to break down the non-fermentable solids and other organic substances into biogas and a treated stillage (i.e., a partially purified liquid) containing far less solids and other substances. The treated stillage, also termed biogas effluent, is returned as backset to the pretreatment apparatus 18. Biogas primarily comprises methane ($CH_4$) and carbon dioxide ($CO_2$), but can also include hydrogen ($H_2$) and trace amounts of other gases such as dihydrogen sulfide ($H_2S$) and ammonia ($NH_3$). Biogas can be combusted for heating or to operate various types of engines to produce mechanical or electrical power.

The main digester 210 can operate at mesophilic temperatures, i.e., between about 35° C. and about 45° C. In one embodiment, the main digester 210 operates at about 40° C. Alternatively, the main digester 210 can operate at thermophilic temperatures, i.e., between about 45° C. and about 65° C. Because the thin stillage coming from the thin stillage tank 26 (i.e., downstream of the first evaporator 22 and the separator 24) is typically at an elevated temperature, the thin stillage feed stream is cooled by a recuperative heat exchanger 202. The heat extracted from the thin stillage feed stream in the heat exchanger 202 is recovered by heating the biogas effluent prior to recycling as a backset to the pretreatment apparatus 18, which can use the additional heat to help drive the pretreatment and fermentation processes. If the recuperative heat exchanger 202 is not capable of sufficiently cooling the thin stillage feed stream, a second heat exchanger 204, using cooling water, provides additional cooling. As illustrated in FIG. 3, the biogas effluent is circulated by a pump 207.

Because the thin stillage is acidic, and because the main digester 210 operates at a neutral pH generally in the range of about 7.0 to about 8.0, the thin stillage feed may be neutralized before being fed into the main digester 210. In one embodiment, ammonia ($NH_3$) is used to neutralize the acidity of the thin stillage feed. The ammonia can be added in an aqueous or an anhydrous form. An advantage of using ammonia is that ammonia used for pH control is also used as a nutrient to aid the yeast in the fermentation process, so ammonia is already available to the ethanol plant system 10 and any difficulties in handling ammonia are already attended to. Additionally, the amount of ammonia required for the biogas apparatus 200 is generally less than is needed for the fermenter 19, so no additional net amount of ammonia need be used; the ammonia (i.e., nitrogen from the ammonia) is recycled back to the front end and provides yeast nutrition during fermentation. In one embodiment, special ammonia-adapted microorganisms can be used in the main digester 210 to provide a stable biogas process. Microorganisms can also be used that are not specially adapted to ammonia, with the understanding that the biogas production of some organisms may be inhibited by ammonia.

As alternatives to ammonia, other neutralizing substances may be used, including lime, sodium hydroxide (NaOH), and magnesium dihydroxide ($Mg(OH)_2$). However, with lime, care must be taken to avoid precipitation in heat exchangers. Also, with NaOH, osmotic stress can be induced in the yeast during fermentation. Further, with $Mg(OH)_2$, struvite precipitation may occur.

In addition to a neutralizing substance, micronutrients may be added to the thin stillage feed to provide nutrition for the microorganisms. In one embodiment of the main digester 210, literally hundreds of different microorganisms are used that together are capable of digesting many materials that yeast cannot break down, including non-fermentable solids, organic acids, oils, salts, and proteins.

During an outage or prolonged shutdown, when a thin stillage feed is not being supplied to the biogas apparatus 200, it may be necessary to provide supplemental heating to the main digester 210 to ensure the health and survival of the microorganisms. For that purpose, an auxiliary steam supply or hot water heating apparatus (not shown) can be provided.

The thin stillage feed rate is set as a percentage of the total volume of the main digester 210 per day, so that fresh feed is continually being combined with partially digested material. In one example, a fresh feed rate of 7% of the volume of the main digester 210 is provided per day. Inevitably, as the fresh feed is mixed with the partially digested material, some fresh feed will flow directed from the inlet to the outlet of the main digester 210. Accordingly, in one embodiment, a post digester 220 is provided downstream of the main digester 210. In other embodiments, any number of anaerobic digesters can be used in the biogas apparatus 200, including one digester or more than two digesters operating in series. The post digester 220 contains the same microorganisms and is smaller than or about the same size as the main digester 210. Both digesters 210 and 220 operate similarly, with a difference being that nearly all of the feed into the post digester 220 (i.e., the secondary feed) is partially digested, while still containing digestible solids and other substances for biogas production. The post digester 200 also provides residence time to minimize discharge of organic solids and acids. For example, if a fresh feed rate of 7% of the volume of the main digester 210 is provided per day, and a secondary feed rate of 10% of the volume of the post digester 220 is provided per day, approximately 0.7% of the secondary feed is fresh feed that has passed through the main digester 210 (i.e., 10% of 7%). Therefore, the post digester 220 greatly decreases the amount of undigested solids and other substances that are returned to the ethanol system 10 as biogas effluent backset. The biogas generated by the post digester 220 is combined with the biogas generated by the main digester 210 to form a biogas stream that is transferred to a dryer by a blower or compressor 230 and is then ready for use as a combustible fuel.

The treated stillage becomes the biogas effluent that is returned to the pretreatment apparatus 18 as backset. In testing using a two-stage digester system (i.e., a main digester 210 and a post digester 220 arranged in series) a biogas composition of 62% methane was achieved, and the amounts of solids and fermentation inhibitors in the stillage were reduced substantially, as shown in Table 1. (In the table, BDL means below the detection limit.)

TABLE 1

|  | Thin Stillage Feed mg/l (ppm) | Main Digester Effluent mg/l (ppm) | Secondary Digester Effluent mg/l (ppm) | Yeast Inhibition Limit mg/l (ppm) | Removal Efficiency % | Detection Limit mg/l (ppm) |
| --- | --- | --- | --- | --- | --- | --- |
| Acetic Acid | 1,190 | 317 | 69 | 600 | 94 | 10 |
| Lactic Acid | 7,700 | BDL | BDL | 6,000 | 100 | 30 |
| Glycerol | 12,006 | BDL | BDL | n/a | 100 | 500 |
| Ethanol | 1,969 | BDL | BDL | n/a | 100 | 100 |
| Total Solids | 6.8% | 2.1% | 1.5% | n/a | 78 | n/a |
| Organic Total Solids | 91.8% | 61.8% | 52.1% | n/a | 87 | n/a |

After one stage of anaerobic digestion, the total solids were reduced in the stillage from 6.8% to 2.1%, or a nearly 70% reduction, while organic total solids (i.e., the percentage of total solids that are organic) was reduced from 91.8% to 61.8%, netting a reduction of nearly 80% in organic solids (i.e., only 61.8% of the remaining 2.1% of solids are organic, as compared with the thin stillage feed having 91.8% of the original 6.8% of solids being organic). The first anaerobic digestion stage also reduced the acetic acid in the stillage from 1190 mg/l to 317 mg/l (a 73% reduction) and virtually eliminated (to below the detection limit) lactic acid, glycerol, and ethanol. Thus, in one stage of anaerobic digestion, the acetic acid and lactic acid were reduced to below the yeast inhibition limit and the total solids and organic solids load of the effluent was substantially reduced.

Further improvement was gained by addition of a second stage of anaerobic digestion. In particular, the total solids were further reduced to 1.5% (a net 78% reduction as compared with the thin stillage feed) and the organic solids were further reduced to 52.1% of the total solids (a net 87% reduction as compared with the thin stillage feed). Also, the acetic acid concentration was further reduced to 69 mg/l, resulting in a net reduction of 94%. Further reductions of lactic acid, glycerol, and ethanol were most likely also achieved in the second stage but were beyond the capacity of the detection equipment to quantify.

In one embodiment, instead of using the biogas effluent directly as backset, the effluent can be further treated using membrane or thermal technology to provide very clean water and a concentrate of solids that could be added back to the evaporators, added to the DDGS dryer, or used separately as a soil enhancement.

Advantages are achieved by reducing the total solids, organic solids, and yeast inhibitors in the biogas effluent that is returned as backset to the fermentation process. First, the reduced concentration of solids and fermentation inhibitors enables the direct backset amount to be increased (i.e., a higher percentage of the direct thin stillage backset from the separator 24 can be used, thus reducing or eliminating the amount of thin stillage that must be sent to the second evaporator 28 and converted to syrup). As a result, a waste stream of syrup, if present, can be reduced or eliminated. Second, the reduction in backset solids enables more corn solids to be added to and processed by the pretreatment apparatus 18 and the fermenter 19, resulting in a greater ethanol production. In particular, more corn enables more ethanol to be produced with the same amount of water flow through the system 10, thereby indirectly reducing the amount of energy required per unit of ethanol produced.

In addition, the biogas apparatus 200 can improve the net energy balance of the ethanol production system 10 by reducing the amount of fossil fuel that must be consumed to produce ethanol. In particular, biogas, which is carbon neutral (i.e., it can be renewably produced by replanting to grow new raw plant materials), can be used to replace natural gas for the boiler 12 and/or the dryer 30. In one embodiment, the biogas apparatus 200 is capable of producing biogas having a heating capacity of about 0.25 to about 0.30 mM BTU/hr per GPM of thin stillage, so that a biogas apparatus 200 processing 80 GPM of thin stillage can produce up to approximately 24 mM BTU/hr of biogas. Further increases in biogas output can be achieved by the addition of syrup to the biogas apparatus 200, as shown for example, by the optional syrup inputs to the biogas apparatus 200 in FIGS. 1, 2a, and 2b, and in FIG. 3. Additionally, the biogas generated by the biogas apparatus 200 can be returned to the ethanol system 10 or can be used to generate electricity or to provide other energy requirements to offset the energy usage by the ethanol system 10. In one embodiment, syrup but not thin stillage is sent to the biogas apparatus 200. In other embodiments, thin stillage and syrup may both be sent to the biogas apparatus 200 in a ratio ranging from about zero (i.e., 100% syrup) to about infinite (i.e., 100% thin stillage).

There is shown in FIG. 2a a schematic diagram and mass balance of water for another embodiment of an ethanol production system 110, including a biogas apparatus 200. Similarly, there is shown in FIG. 2b a schematic diagram and mass balance of water for a further embodiment of an ethanol production system 410, the system 410 being a variant of the system 110. The biogas apparatus 200 can be integrated with either of the ethanol production systems 110 and 410.

In the ethanol production system 110, fresh water is provided to a scrubber 114 for removing ethanol from the fermentation off-gas. Corn is fed into a pretreatment apparatus 118 for pretreatment, accompanied in the depicted embodiment by an amount of water. Additional water is provided to the pretreatment apparatus 118 from the boiler 112 in the form of steam to aid the pretreatment. The resultant mash proceeds to a fermenter 119 where yeast is added to drive the fermentation process. Additional amounts of water are provided to the pretreatment apparatus 118 as direct thin stillage backset from a centrifugal separator 124, condensed vapor from an evaporator 128, byproduct water from a methanator 140, and effluent backset from the biogas apparatus 200.

Ethanol is produced by the fermentation of the fermentable portions of the corn, i.e., the portions of the corn that can be converter to sugar and fermented by yeast. Exiting the fermenter 119 is a beer including the ethanol, water, solids, dissolved solids, and other substances such as organic acids, oils, proteins, and salts. The beer is distilled in a distillation apparatus 120 to extract the ethanol as vapor, leaving a whole stillage that contains the solids and other substances. The ethanol can be further purified by dehydration, e.g., using a molecular sieve. An amount of water is also returned via a side stripper to the pretreatment apparatus 118. The whole stillage is next separated in a separator 124 such as one or more centrifuges to produce a thin stillage and wet distillers grains (WDG). Although the larger solids are removed in the WDG, the thin stillage still includes fine solids and solubles, as well as other dissolved and suspended substances.

The thin stillage is apportioned between a portion returned to the pretreatment apparatus 118 (i.e., direct backset), a portion sent to an evaporator 128, and a portion sent to the biogas apparatus 200. In particular, the amount of thin stillage returned to the pretreatment apparatus 118 as direct backset is reduced by the amount of thin stillage sent to the biogas apparatus 200. The evaporator 128 produces a syrup, which has been concentrated from the thin stillage to have a substantially higher percentage of fine solids and other substances. In the illustrated embodiment, another stream exiting the evaporator 128 goes to a methanator 140, which biologically converts acids in the stream to methane, and then returns the residual stream (with reduced acids) to the pretreatment apparatus 118. The WDG and syrup are combined in a dryer 130, in which the water is driven off and exhausted and the solids are dried for sale. (It is understood that the WDG and syrup are dried only if there is a market for the resultant DDGS; otherwise, it would not be worth the cost of operating the dryer 130.)

In the ethanol production system 410, fresh water is provided to a scrubber 414 for removing ethanol from the fermentation off-gas. Corn is fed into a pretreatment apparatus 418 for pretreatment, accompanied in the depicted embodiment by an amount of water. Additional water is provided to the pretreatment apparatus 418 from the boiler 412 in the form of steam to aid the pretreatment. The resultant mash proceeds to a fermenter 419 where yeast is added to drive the fermentation process. Additional amounts of water are provided to the pretreatment apparatus 418 as direct thin stillage backset from a centrifugal separator 424, steam from an evaporator 428, byproduct water from a methanator 440, and effluent backset from the biogas apparatus 200.

Ethanol is produced by the fermentation of the fermentable portions of the corn, i.e., the portions of the corn that can be converter to sugar and fermented by yeast. Exiting the fermenter 419 is a beer including the ethanol, water, solids, dissolved solids, and other substances such as organic acids, oils, proteins, and salts. The beer is distilled in a distillation apparatus 420 to extract the ethanol as vapor, leaving a whole stillage that contains the solids and other substances. The ethanol can be further purified by dehydration, e.g., using a molecular sieve. An amount of water is also returned via a side stripper to the pretreatment apparatus 418. The whole stillage is next separated in a separator 424 such as one or more centrifuges to produce a thin stillage and wet distillers grains (WDG). Although the larger solids are removed in the WDG, the thin stillage still includes fine solids and solubles, as well as other dissolved and suspended substances.

The thin stillage is apportioned between a portion returned to the pretreatment apparatus 418 (i.e., direct backset), a portion sent to an evaporator 428, and a portion sent to the biogas apparatus 200. In particular, the amount of thin stillage sent to the evaporator 428 is reduced by the amount of thin stillage sent to the biogas apparatus 200. The evaporator 428 produces a syrup, which has been concentrated from the thin stillage to have a substantially higher percentage of fine solids and other substances. In the illustrated embodiment, another stream exiting the evaporator 428 goes to a methanator 440, which biologically converts acids in the stream to methane, and then returns the residual stream (with reduced acids) to the pretreatment apparatus 418. The WDG and syrup are combined in a dryer 430, in which the water is driven off and exhausted and the solids are dried for sale.

The biogas apparatus 200 operates as described above in conjunction with the system 110 or 410 to convert the thin stillage into a biogas usable to produce energy by combustion, and also to produced a treated thin stillage that can be returned to the pretreatment apparatus 118 or 418, respectively, as a biogas effluent.

The schematics of FIGS. 2a and 2b include water flow amounts based on an exemplary 60 mM gallons per year production of ethanol, a first set of numbers (not in square brackets) designating the water flow at various points of an existing process when a biogas apparatus 200 is not employed, and a second set of numbers (in square brackets) designating the water flow at the same points of the presently disclosed process when a biogas apparatus 200 is employed. As described in detail below, an exemplary system 110 using a biogas apparatus 200 saves about 5 GPM of water and about 21.5 mM BTU/hr of energy, and allows for increased fermentable solids to be added to the system 110, as compared with a comparable system not using a biogas apparatus 200. Similarly, an exemplary system 410 using a biogas apparatus 200 saves about 6 GPM of water and about 21.5 mM BTU/hr of energy, and allows for the use of a lower capacity evaporator and dryer, or eliminates an evaporator or dryer bottleneck.

With reference to FIG. 2a, in operating the exemplary system 110 without the biogas apparatus 200, a fresh water flow rate of 269 GPM is required, and 142 GPM is exhausted by the dryer. By comparison, in a system with the biogas apparatus 200, a fresh water flow rate of 264 GPM is required, a net savings of 5 GPM, while only 131 GPM is exhausted out the stack by the dryer 130 (a savings of 11 GPM); an additional 5 GPM is consumed by the biogas apparatus 200 in making the biogas. In sum, a net water savings of about 2% can be realized for the exemplary plant, which equates to about 7,200 gallons per day or 2.6 million gallons per year, based on 8,400 operating hours per year.

A comparison of the water flows provided to the pretreatment apparatus 118 indicates that about the same amount of water or liquids is provided to the pretreatment apparatus 118 when a biogas apparatus 200 is used as when no biogas apparatus 200 is used. However, the efficiency of processing corn into ethanol, and ultimately the amount of corn that can be processed into ethanol, can be increased because the water and liquids being provided to the pretreatment apparatus 118 and the fermenter 119 are, on the whole, of better quality for fermentation. In particular, the liquids being provided to the fermenter 119 have less non-fermentable solids and less fermentation inhibiting substances that would otherwise reduce the effectiveness of the yeast fermentation, as a result of the partial purification of thin stillage by the anaerobic digesters 210 and 220.

In a system 110 without a biogas apparatus 200, 75 GPM of water is provided to the pretreatment apparatus 118 from the scrubber 114, 42 GPM of water with the corn, 37 GPM from the boiler 112, 248 GPM of water as thin stillage backset, and 177 GPM of water as backset from the methanator 140, for a total of 579 GPM of water. Water is removed by the evaporator 128 from the 379 GPM of thin stillage, the byproduct of which is 51 GPM of water in the syrup. Some of the steam generated by the evaporator 128 is used to provide heat for distillation, and the condensate is treated in the methanator 140. Also, the separator 124 produces 91 GPM of water with the WDG. When the combination of WDG and syrup is dried, 142 GPM of water is exhausted from the system.

In a system 110 with the biogas apparatus 200, the same amount of water is provided with the corn and from the boiler 112, and the thin stillage flow to the evaporator 128 remains at 379 GPM, while the scrubber water is reduced by 5 GPM to 70 GPM, the methanator backset is increased by 10 GPM to 187 GPM, and the direct backset is reduced by 80 GPM to 168 GPM. Also, 80 GPM of thin stillage is diverted from the direct backset to the biogas apparatus 200, and 75 GPM of biogas effluent is returned as backset from the biogas apparatus 200 to the pretreatment apparatus 118. In net, 75 GPM less water is returned to the pretreatment apparatus 118 from the methanator 140, the evaporator 128, and the scrubber 114. The difference is made up from the biogas apparatus 200, which uses 80 GPM of thin stillage to produce biogas containing 5 GPM of water, and returns 75 GPM of treated (partially purified) thin stillage to the pretreatment apparatus 118.

With reference to FIG. 2b, in operating the exemplary system 410 without the biogas apparatus 200, a fresh water flow rate of 269 GPM is required, and 142 GPM is exhausted by the dryer 430. By comparison, in a system with the biogas apparatus 200, a fresh water flow rate of 263 GPM is required, a net savings of 6 GPM, while only 131 GPM is exhausted out the stack by the dryer 430 (a savings of 11 GPM); an additional 5 GPM is consumed by the biogas apparatus 200 in making the biogas.

A comparison of the water flows provided to the pretreatment apparatus 418 indicates that about the same amount of water or liquids is provided to the pretreatment apparatus 418 when a biogas apparatus 200 is used as when no biogas apparatus 200 is used. However, by reducing the amount of thin stillage sent to the evaporator 428, the load on the evaporator 428 and consequently on the dryer 430 can be reduced, enabling the system 410 to produce more ethanol without increasing the capital expenditure for larger equipment. In particular, a portion of the thin stillage that would otherwise be evaporated to produce syrup is diverted to the biogas apparatus, partially purified by the anaerobic digesters 210 and 220, and returned to the pretreatment apparatus 418.

In a system 410 without a biogas apparatus 200, 75 GPM of water is provided to the pretreatment apparatus 418 from the scrubber 414, 42 GPM of water with the corn, 37 GPM from the boiler 112, 248 GPM of water as thin stillage backset, and 177 GPM of water as backset from the methanator 140, for a total of 579 GPM of water. Water is removed by the evaporator 128 from 379 GPM of thin stillage, the byproduct of which is 51 GPM of water in the syrup. Some of the steam generated by the evaporator 128 is used to provide heat for distillation, and the condensate is treated in the methanator 140. Also, the separator 124 produces 91 GPM of water with the WDG. When the combination of WDG and syrup is dried, 142 GPM of water is exhausted from the system.

In a system 410 with the biogas apparatus 200, the same amount of water is provided with the corn and from the boiler 112, and the thin stillage direct backset flow rate of 248 GPM remains the same, while the scrubber water is reduced by 6 GPM to 69 GPM and the methanator backset is reduced by 69 GPM to 108 GPM. The amount of thin stillage supplied to the evaporator 428 is reduced by 80 GPM to 299 GPM, providing 80 GPM of thin stillage to the biogas apparatus 200 instead. In net, about 75 GPM less water is returned to the pretreatment apparatus 418 from the methanator 440, the evaporator 428, and the scrubber 414. The difference is made up from the biogas apparatus 200, which uses 80 GPM of thin stillage to produce biogas containing 5 GPM of water, and returns 75 GPM of treated (partially purified) thin stillage to the pretreatment apparatus 418.

In one embodiment of the exemplary system 410, the non-biogas system may be limited by the size of the evaporator 428. Thus, by adding the biogas apparatus 200, the load of the evaporator is reduced by 80 GPM (from 374 GPM thin stillage to 294 GPM), or by about 21%, so that the existing evaporator 128 can be used even with a higher front end production rate and the fermentation process can be improved by the removal of fine solids and fermentation inhibitors from the treated thin stillage. Further, the evaporator produces 10 GPM less water in the form of syrup that must be dried (41 GPM instead of 51 GPM), reducing the energy consumption of the dryer 130 by 7.2 mM BTU/hr, and reducing the amount of water exhausted out the stack by 11 GPM. Additionally, the biogas produced by the biogas apparatus 200 has a thermal value of 21.5 mM BTU/hr (which can be used, e.g., to fire a boiler or dryer), resulting in an aggregate energy savings of 28.7 mM BTU/hr.

As disclosed herein, systems and processes are provided for improving the energy efficiency, reducing the fresh water usage, reducing or eliminating waste streams, and improving the productivity of an ethanol production system and process. In particular, several problems or limitations with existing ethanol production systems can be solved by the systems and processes disclosed herein.

Existing ethanol plants may suffer from a backset limitation, wherein only a limited quantity of thin stillage can be used as backset because of the non-fermentable solids and fermentation inhibitors (e.g., acids that inhibit functioning of the yeast) that are contained in the thin stillage. In cases where the backset available from thin stillage is insufficient, an ethanol plant can experience water balance problems requiring increased fresh water supply and resulting in liquid discharge of a portion of the thin stillage or syrup. This is particularly problematic because the thin stillage has a high chemical oxygen demand (COD) that is in excess of permissible discharge limits. Moreover, for zero discharge plants, no such high COD liquid may be discharged. In some cases, discharge of syrup (i.e., concentrated thin stillage) may be possible, but more often syrup is not even salable and must be given away for free or disposed of at a cost.

Some existing ethanol plants use a methanator (e.g., as shown in FIGS. 2a and 2b, elements 140 and 440, respectively) to clean up evaporator condensate by converting organic acids into biogas consisting primarily of methane ($CH_4$) and carbon dioxide ($CO_2$), thus reducing the concentration of fermentation inhibitors and allowing higher backset flow amounts. However, the biogas output of a methanator, and thus the natural gas offset potential of a methanator, is much lower than is achieved by the anaerobic digester system disclosed herein. In particular, because the methanator processes a relatively clean stream of condensate (i.e., having virtually no solids and only treating organic acids which are fermentation inhibitors) from the evaporator, as compared with the relatively dirty stream of thin stillage (i.e., having a relatively high loading of non-fermentable solids and fermentation inhibitors) from the separator that is processed by the biogas apparatus, the amount of energy available from the methanator is far less than from an anaerobic digester.

Thus, the presently disclosed systems and processes resolve the backset limitation by anaerobically digesting thin stillage, first converting non-fermentable solids into organic acids and then converting the acids into methane. By optimizing operating parameters of the anaerobic digesters, such as the residence time of the thin stillage and the type and quantity of nutrients and pH neutralizers, the organic acid load of the biogas effluent backset can be reduced by as much as 90%, thereby keeping the organic acid load of the biogas effluent backset below fermentation stress levels. The reduction in yeast or fermentation stressing agents allows for an increase in the amount of backset while improving fermentation performance as compared with a system using only untreated thin stillage backset. As a result, the fermentation activity of the yeast is more efficient, allowing for greater throughput of raw plant materials and increased ethanol production yields from the same equipment.

Further, existing ethanol plants suffer from a limitation on the concentration of fermentable solids that can be input to the pretreatment apparatus and fermenter as a result of the non-fermentable solids recycled to the pretreatment apparatus and fermenter in the thin stillage backset. The disclosed systems and methods substantially remedy this problem by anaerobically digesting a large portion of the solids from the thin stillage and returning a biogas effluent backset to the pretreatment apparatus with a far lower non-fermentable solids content. In particular, biogas is generated from the organic content of the thin stillage, typically reducing the total solids by between about 50% and about 80%. Therefore, by reducing the non-fermentable solids loading in the pretreatment apparatus and fermenter, additional fermentable solids (i.e., additional raw plant materials) can be added, resulting in increased ethanol production yields from the same equipment.

Additionally, some existing ethanol plants suffer from an evaporator throughput limitation, wherein even if the plant could process more raw plant materials and produce more ethanol in the front end (i.e., in the pretreatment apparatus and fermenter), the capacity of the evaporator to handle more thin stillage evaporation is reached. In such situations, the capital cost of upgrading the size of the evaporator is substantial and is often cost prohibitive because the increased productivity cannot support a reasonable return on equity. The systems and processes disclosed herein overcome such evaporator limitations by diverting a portion of the thin stillage to the anaerobic digesters, thus reducing the flow of thin stillage to the evaporator and freeing up evaporator capacity. Also, reduction of acid inhibitors and non-fermentable solids in the biogas effluent backset allows for an increase in the total amount of thin stillage recycled as backset, further reducing evaporator loading.

Still further, some existing ethanol plants suffer from a dryer throughput limitation, wherein even if the plant could process more raw plant materials and produce more ethanol in the front end (i.e., in the pretreatment apparatus and fermenter), the capacity of the dryer to handle more wet distillers grains and/or syrup is reached. In such situations, the capital cost of upgrading the size of the dryer is substantial and is often cost prohibitive because the increased productivity cannot support a reasonable return on equity. The systems and processes disclosed herein overcome dryer limitations by diverting a portion of the thin stillage to the anaerobic digesters, thus reducing the amount of syrup produced by concentrating the thin stillage in the evaporator, thereby freeing up dryer capacity.

In sum, existing ethanol plants may be limited in ways that inhibit maximum ethanol production, or that cause plants to give away for free byproducts such as syrup that may have residual energy value, or that require costs for the disposal of high COD water that has residual energy value. The systems and process disclosed herein reduce or eliminate the production of syrup, and enable high COD water to be treated in the anaerobic digesters and then recycled as backset, thus eliminating the need for discharge of syrup and high COD water.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. An integrated apparatus for producing ethanol and biogas from raw plant materials, the integrated apparatus comprising:
   a pretreatment apparatus for converting raw plant materials into sugars, the pretreatment apparatus being supplied with an amount of fresh water and an amount of backset;
   a fermenter including yeast for fermenting the sugars to produce a beer comprising ethanol;
   a distillation apparatus for separating the beer into the ethanol and a whole stillage;
   a separator for separating the whole stillage into a thin stillage and wet distillers grains, the thin stillage comprising non-fermentable solids and organic acids;
   a thin stillage tank for collection of the thin stillage, the thin stillage tank having a first supply and a second supply extending therefrom, the first supply comprising a backset return supply extending into the pretreatment apparatus and the second supply comprising a biogas supply, wherein the thin stillage tank is operable to allow for selective distribution of thin stillage to vary flow rates to the backset return supply and the biogas supply to increase: (i) the production of ethanol for the same or less water and energy requirement, (ii) an amount of raw plant material feed directed to the pretreatment apparatus, and (iii) an amount of thin stillage fed to the backset directly from the thin stillage tank; and a biogas apparatus for processing a first portion of the thin stillage to produce biogas and a biogas effluent, the biogas apparatus receiving the first portion of thin stillage from the thin stillage tank biogas supply, the biogas apparatus converting a percentage of the non-fermentable solids and organic acids in the thin stillage into biogas and thereby reducing the concentration of the non-fermentable solids and organic acids in the biogas effluent, wherein the biogas apparatus comprises a biogas discharge and a biogas effluent return, the biogas effluent return extends from the biogas apparatus into the backset return supply and into the pretreatment apparatus, resulting in an integrated apparatus that produces ethanol, biogas and byproducts that are recycled into the integrated apparatus at the pretreatment apparatus, and no thin stillage discharge extends from the integrated apparatus.

2. The integrated apparatus of claim 1, the biogas apparatus comprising at least one anaerobic digester having microorganisms for processing the thin stillage.

3. The integrated apparatus of claim 2, wherein a pH of the at least one digester is controlled by addition of a neutralizing agent.

4. The integrated apparatus of claim 3, wherein the neutralizing agent is ammonia, wherein the microorganisms are adapted for an ammonia environment.

5. The integrated apparatus of claim 4, wherein nitrogen from the ammonia added as a neutralizing agent and additional ammonia generated by digestion of the organic acids is recycled via the biogas effluent return as a nutrient for the yeast in fermentation, thereby reducing or eliminating the need for a separate addition of ammonia to the fermenter.

6. The integrated apparatus of claim 2, the biogas apparatus comprising a main anaerobic digester and a secondary anaerobic digester in series.

7. The integrated apparatus of claim 2, the biogas apparatus further comprising a recuperative heat exchanger for cooling the thin stillage prior to entering the at least one digester and for reheating the biogas effluent prior to being recycled to the pretreatment apparatus.

8. The integrated apparatus of claim 1, wherein a second portion of the thin stillage is recycled directly as backset from the separator to the pretreatment apparatus; and
wherein an increase in the amount of backset obtained by recycling the biogas effluent from the biogas apparatus reduces the amount of fresh water supplied to the pretreatment apparatus.

9. The integrated apparatus of claim 1, wherein a second portion of the thin stillage is recycled directly as backset from the separator to the pretreatment apparatus; and
wherein an increase in the amount of backset obtained by recycling the biogas effluent from the biogas apparatus reduces the amount of the second portion of the thin stillage recycled directly as backset, reducing the amount of solids returned to the pretreatment apparatus so that more raw plant materials can be added to the pretreatment apparatus.

10. The integrated apparatus of claim 1, further comprising an evaporator for concentrating a third portion of the thin stillage into a syrup by boiling off vapor from the thin stillage;
wherein a portion of the syrup is further provided to the biogas apparatus for processing into biogas and biogas effluent, the syrup and the first portion of thin stillage being provided to the biogas apparatus in any ratio.

11. The integrated apparatus of claim 1, further comprising an evaporator for concentrating a third portion of the thin stillage into a syrup by boiling off vapor from the thin stillage;
wherein the backset further comprises the vapor boiled off from the thin stillage;
wherein an increase in the amount of backset obtained by recycling the biogas effluent from the biogas apparatus reduces the third portion of the thin stillage that must be concentrated by the evaporator, thereby reducing the energy loading of the evaporator; and
wherein a reduction in the third portion of the thin stillage reduces the amount of the syrup.

12. The integrated apparatus of claim 11, further comprising a dryer for drying the wet distillers grains and the syrup;
wherein an increase in the amount of backset obtained by recycling the biogas effluent from the biogas apparatus reduces the energy loading of the dryer by reducing the amount of the syrup that must be dried.

13. The integrated apparatus of claim 11, further comprising a dryer for drying the wet distillers grains and the syrup;
wherein an increase in the amount of backset obtained by recycling the biogas effluent from the biogas apparatus reduces or eliminates the syrup load-out from the system.

14. An integrated apparatus for producing ethanol and biogas from raw plant materials, the integrated apparatus comprising:
a pretreatment apparatus for converting raw plant materials into sugars, the pretreatment apparatus being supplied with an amount of fresh water or and an amount of backset;
a fermenter including yeast for fermenting the sugars to produce a beer comprising ethanol;
a distillation apparatus for separating the beer into the ethanol and a whole stillage;
a separator for separating the whole stillage into a thin stillage and wet distillers grains, the thin stillage comprising non-fermentable solids and organic acids;
a thin stillage tank for collection of the thin stillage, the thin stillage tank having a first backset return supply extending therefrom into the pretreatment apparatus and a second biogas supply extending therefrom, wherein the thin stillage tank is operable to allow for selective distribution of thin stillage to vary flow rates to the backset return and the biogas supply to increase: (i) the production of ethanol for the same or less water and energy requirement, (ii) an amount of raw plant material feed directed to the pretreatment apparatus, and (iii) an amount of thin stillage fed to the backset directly from the thin stillage tank;
an evaporator for concentrating a first portion of the thin stillage into a syrup by boiling off vapor from the thin stillage; and
a biogas apparatus for processing at least one of a portion of the syrup and a second portion of the thin stillage to produce biogas and a biogas effluent, the biogas apparatus converting a percentage of the non-fermentable solids and organic acids in the syrup and the thin stillage into biogas and thereby reducing the concentration of the non-fermentable solids and organic acids in the biogas effluent;

wherein the biogas apparatus comprises a biogas discharge and a biogas effluent return, the biogas effluent return extends from the biogas apparatus into the backset return and into the pretreatment apparatus, resulting in a system that produces ethanol, biogas and byproducts that are recycled into the integrated apparatus at the pretreatment apparatus, and no thin stillage discharge extends from the integrated apparatus.

15. The integrated apparatus of claim 14, wherein the syrup and the thin stillage are provided to the biogas apparatus in any ratio.

16. The integrated apparatus of claim 14, the biogas apparatus comprising at least one anaerobic digester having microorganisms for processing the thin stillage;

wherein a pH of the at least one digester is controlled by addition of ammonia as a neutralizing agent; and wherein the microorganisms are adapted for an ammonia environment.

17. The integrated apparatus of claim 14, wherein a third portion of the thin stillage is recycled directly as backset from the separator to the pretreatment apparatus; and wherein an increase in the amount of backset obtained by recycling the biogas effluent from the biogas apparatus reduces the amount of fresh water supplied to the pretreatment apparatus.

18. The integrated apparatus of claim 14, wherein a third portion of the thin stillage is recycled directly as backset from the separator to the pretreatment apparatus; and wherein an increase in the amount of backset obtained by recycling the biogas effluent from the biogas apparatus reduces the amount of the third portion of the thin stillage recycled directly as backset, reducing the amount of solids returned to the pretreatment apparatus so that more raw plant materials can be added to the pretreatment apparatus.

19. The integrated apparatus of claim 14, wherein the backset further comprises the vapor boiled off from the thin stillage;

wherein an increase in the amount of backset obtained by recycling the biogas effluent from the biogas apparatus reduces the first portion of the thin stillage that must be concentrated by the evaporator, thereby reducing the energy loading of the evaporator; and wherein a reduction in the first portion of the thin stillage reduces the amount of the syrup.

20. The integrated apparatus of claim 14, further comprising a dryer for drying the wet distillers grains and the syrup;

wherein an increase in the amount of backset obtained by recycling the biogas effluent from the biogas apparatus reduces the energy loading of the dryer by reducing the amount of the syrup that must be dried.

21. The integrated apparatus of claim 14, further comprising a dryer for drying the wet distillers grains and the syrup;

wherein an increase in the amount of backset obtained by recycling the biogas effluent from the biogas apparatus reduces or eliminates the syrup load-out from the system.

22. An integrated apparatus for producing ethanol and biogas from raw plant materials, the integrated apparatus comprising:

a pretreatment apparatus for converting raw plant materials into sugars, the pretreatment apparatus being supplied with an amount of fresh water and an amount of backset;

a fermenter including yeast for fermenting the sugars to produce a beer comprising ethanol;

a distillation apparatus for separating the beer into the ethanol and a whole stillage;

a separator for separating the whole stillage into a thin stillage and wet distillers grains, the thin stillage comprising non-fermentable solids and organic acids;

a thin stillage tank for collection of the thin stillage, the thin stillage tank having a first backset return supply, and a second biogas supply extending therefrom, the first backset return supply extending into the pretreatment apparatus and the second biogas supply extending into a biogas apparatus for processing a portion of the thin stillage to produce biogas and a biogas effluent, wherein the biogas apparatus comprises a biogas discharge and a biogas effluent return, the biogas effluent return extends from the biogas apparatus into the backset return, and no thin stillage discharge extends from the integrated apparatus.

\* \* \* \* \*